US012702149B2

(12) United States Patent
Antony

(10) Patent No.: US 12,702,149 B2
(45) Date of Patent: Aug. 11, 2026

(54) RESISTANT STARCH FROM NATURAL SOURCES AND THEIR PREPARATION

(71) Applicant: Arjuna Natural Private Limited, Kerala (IN)

(72) Inventor: Benny Antony, Kerala (IN)

(73) Assignee: ARJUNA NATURAL PRIVATE LIMITED, Aluva (IN)

( * ) Notice: Subject to any disclaimer, the term of this patent is extended or adjusted under 35 U.S.C. 154(b) by 841 days.

(21) Appl. No.: 17/784,519

(22) PCT Filed: Dec. 18, 2020

(86) PCT No.: PCT/IB2020/062182

§ 371 (c)(1),
(2) Date: Jun. 10, 2022

(87) PCT Pub. No.: WO2021/124246

PCT Pub. Date: Jun. 24, 2021

(65) Prior Publication Data

US 2023/0033784 A1 Feb. 2, 2023

(30) Foreign Application Priority Data

Dec. 19, 2019 (IN) ............................ 201941052987

(51) Int. Cl.
*A23L 33/22* (2016.01)
*A23L 29/219* (2016.01)
(Continued)

(52) U.S. Cl.
CPC ............ *A23L 33/22* (2016.08); *A23L 29/219* (2016.08); *A23L 33/105* (2016.08); *A23L 33/30* (2016.08); *A61K 36/9066* (2013.01); *A61P 3/02* (2018.01)

(58) Field of Classification Search
CPC ........ A23L 33/30; A23L 33/22; A23L 33/105; A61K 36/9066
See application file for complete search history.

(56) References Cited

U.S. PATENT DOCUMENTS 5,792,754 A * 8/1998 Green .................. A23L 29/231 514/23
6,838,099 B2 1/2005 Woo et al.
2014/0010903 A1* 1/2014 Madhavamenon .. A61K 9/0095 424/756

FOREIGN PATENT DOCUMENTS

EP 2086349 B1 11/2012
WO 2008/062057 A1 5/2008
(Continued)

OTHER PUBLICATIONS

Chawla et al., "Soluble Dietary Fiber", Comprehensive Reviews in Food Science and Food Safety, vol. 9, (2010), pp. 178-196. (Year: 2010).*
(Continued)

*Primary Examiner* — Elizabeth Gwartney
(74) *Attorney, Agent, or Firm* — Venable LLP; Keith G. Haddaway; Hemant Khanna

(57) ABSTRACT

The invention relates to a dietary fiber rich composition derived from plants parts, preferably from ginger, turmeric and Emblica. The composition has at least 45% dietary fiber and most of it is insoluble fibre. The insoluble fibre mostly comprises of resistant starch, the composition has at least 15% resistant starch. The invention also relates to a method of extracting and enrichment of fibre from plant parts. The method further includes solvent extraction, acid treatment and enzymatic treatment. The Starch in the composition either enriched and/or chemical modified. The composition has a place in novel food products, for food processing purposes, as functional food, dietary supplementation pur-
(Continued)

poses and pharmaceutical preparations. Composition has clinically significant activity towards fat loss, blood glucose regulation, inhibiting inflammation and enhance bioavailability.

14 Claims, 3 Drawing Sheets

(51) Int. Cl.

| | |
|---|---|
| ***A23L 33/00*** | (2016.01) |
| ***A23L 33/105*** | (2016.01) |
| ***A61K 36/9066*** | (2006.01) |
| ***A61P 3/02*** | (2006.01) |

(56) References Cited

FOREIGN PATENT DOCUMENTS

| | | | | |
|---|---|---|---|---|
| WO | 2015/099842 A1 | | 7/2015 | |
| WO | WO-2019022991 A1 | * | 1/2019 | ........... A61K 31/198 |

OTHER PUBLICATIONS

Ikpeama et al., "Nutritional Composition of Tumeric (Curcuma longa) and its Antimicrobial Properties", International Journal of Scientific & Engineering Research, vol. 4, Issue 10, (Oct. 2014), pp. 1085-1089. (Year: 2014).*

Lv et al., "Chemical composition and functional characteristics of dietary fiber-rich powder obtained from core of maize straw", Food Chemistry, 227, (2017), pp. 383-389. (Year: 2017).*

Marín et al., By-products from different citrus processes as a source of customized functional fibres, Food Chemistry, 100, (2007), pp. 736-741. (Year: 2007).*

International Search Report and Written Opinion isssued in corresponding International Application No. PCT/IB2020/062182 on Apr. 20, 2021.

* cited by examiner

RESISTANT STARCH FROM NATURAL SOURCES AND THEIR PREPARATION

CROSS-REFERENCE TO RELATED APPLICATIONS

This application is a U.S. National Stage Application of PCT/IB2020/062182, filed Dec. 18, 2020, which claims priority benefit from Indian Patent Application number 201941052987, filed on Dec. 19, 2019, the entire content of which is incorporated herein by reference.

FIELD OF INVENTION

The invention relates to dietary fibre derived from plants, their process of extraction and treatment. The invention further relates to the use of such dietary fibre in medicinal preparations and treatment. The invention further relates to medicinal formations with dietary fibre and medicinal plants, minerals and nutrients.

BACKGROUND OF THE INVENTION

Dietary fibre is a class of carbohydrates that are important in overall health. Dietary fibre is a term that refers to a group of food constituents that pass undigested through the stomach and the small intestine and reach the large intestine virtually unchanged. It is made up of indigestible parts of plants and is mainly composed of different types of non-starch polysaccharides (NSP), resistant starch and lignin.

Naturally occurring fibre (often referred to as “intrinsic”) occurs in foods such as vegetables, whole grains, fruits, cereal bran, flaked cereal and flours. The fibres are also considered to be “intact” because they have not been removed from the food. Foods containing these fibres have been shown to provide beneficial physiological effects to human health.

Soluble dietary fibre (SDF) and insoluble dietary fibres (IDF) make up the two basic categories of dietary fibre. IDFs primarily consist of cellulose, hemicelluloses, resistant starch, and lignin. SDFs include oligosaccharides, including fructo oligosaccharide (FOS), pectins, 3 glucans (oat and barley grains), galactomannan gums, alginate, and *psyllium.*

All starches are composed of two types of polysaccharides: amylose and amylopectin. Amylopectin is highly branched, leaving more surface area available for digestion. Amylopectin is broken down quickly, which means it produces a larger rise in blood sugar (glucose) and subsequently, a large rise in insulin. Amylose is a straight chain polysaccharide, having less surface area exposed for digestion. Foods high in amylose are digested more slowly. They are less likely to spike blood glucose or insulin. More than 50% of calorific requirement of human diet is fulfilled by starch based foods, and quantity of starch-based food affects overall blood glucose and homeostasis in humans. Starches are long chains of glucose that are found in grains, potatoes and various foods.

While most starches are broken down by enzymes in our small intestine into sugar, which is then absorbed into the blood, so a fully absorption of starch is not possible. Starch is classified as rapidly digestible starch (RDS), slowly digestible starch (SDS) and resistant starch (RS). Both RDS and SDS are completely digested in the small intestine. Resistant starch (RS) is defined as a portion of starch that survives digestion in the small intestine of healthy humans, but is fermented in the colon. When RS is fermented in the large intestine, short chain fatty acids (SCFA) such as acetate, butyrate and propionate, along with gases are produced. SCFAs can be absorbed into the body from the colon and used by colonic bacteria for energy. Enzyme resistant starch behaves like dietary fibre, both physiologically and analytically. It is fermented in the large intestine and helps to prevent digestive and colon disorders by acting as prebiotic for intestinal flora (probiotic). Sources of resistant starch include whole grains, legumes, cooked and chilled pasta, potatoes, rice and green bananas.

Not all resistant starches are the same. There are 5 different types.

Type 1: Encapsulated starch found in grains, seeds and legumes that resists digestion because it is bound within the fibrous cell walls.

Type 2: Resistant granules found in some starchy foods, including raw potatoes, green (unripe) bananas and high amylase maize starch.

Type 3: Retrograded starch formed when certain starchy foods, including potatoes and rice, are cooked and then cooled. The cooling turns some of the digestible starches into resistant starches via retrogradation.

Type 4: Chemically modified Starch is formed via a chemical process.

Type 5: Amylose-lipid complex characterised by a lipid component complexed with amylose.

Present application discloses a composition derived from natural sources contains soluble and insoluble part of dietary fibre, starch, modified starch, starch derivatives. Present application also discloses composition derived from natural sources contains soluble and insoluble part of dietary fibre, starch, modified starch, starch derivatives for enhancing the bioavailability and bioactivity of poor bioavailable substances.

Curcumin, a compound found in turmeric has well established medicinal properties and is well known to be pharmaceutically safe. Curcumin is among the few agents to block both the COX and LOX (lipoxygenase) pathways of inflammation and carcinogenesis by directly modulating arachidonic acid metabolism. From cancer to inflammation to curcumin’s antioxidative properties is well established in many clinical trials. Same is true for curcumin analogues, Bisdemethoxycurcumin and Demethoxycurcumin are also known from their medical properties. A limitation to use of curcumin is its poor bioavailability. Multiple studies on animals and humans have shown the poor bioavailability of curcumin in blood and brain when administered orally. In rodents, curcumin demonstrates poor systemic bioavailability after p.o. dosing (Ireson, C. R. et al, Cancer Res., 2001, 41:1058-64) which may be related to its inadequate absorption and fast metabolism. Curcumin bioavailability may also be poor in humans as seen from the results of a pilot study of a standardized turmeric extract in colorectal cancer patients (Sharma, R. A. et al, Clin. Cancer Res., 2001, 7:1834-1900).

Improving the bioavailability is a tall challenge that has to be overcome to use curcumin more extensively for medicinal purposes. There are few formulations and compositions that have shown some progress in this field. Use of nano-crystalline curcumin or nano-emulsion as shown in CN106038488B and CN109745291A, focuses on improving the solubility of curcumin so that it could be absorbed before it metabolises in the gastrointestinal tract. Another method of enhancing the bioavailability of curcumin is by adding it with lipids to improve its solubility and in turn bioavailability, for example, blending curcumin with piperine or with essential oil of turmeric as shown in CA2247467C and WO2014068597A3.

The present invention discloses a novel method of extracting dietary fibre from plants and also a method to enrich resistant starch. The present application discloses an alternative method of enhancing the bioavailability of curcuminoids, by delivering curcuminoids on a carrier and reducing metabolism of curcuminoids.

OBJECT OF THE INVENTION

The primary object of the invention is to make a dietary fibre composition with purity of about 40% to 95% and resistant starch with a purity of 15% to 75%.

Another object of the invention is to form medicinal composition using dietary fibre composition and other plant extracts.

Yet another objective is the method of preparation of dietary fibre from plant parts.

SUMMARY OF THE INVENTION

The following presents a simplified summary of the disclosure in order to provide a basic understanding of some aspects of the disclosure. This summary is not an extensive overview. It is not intended to identify the key/critical elements of the disclosure or to delineate the scope of the disclosure. Its sole purpose is to present some concept of the disclosure in a simplified form as a prelude to a more detailed description of the disclosure presented later.

The main object of the present disclosure is to present a dietary fibre composition derived from plant source comprising at least 40% dietary fibre by weight. The dietary fibre comprises soluble fibre and insoluble fibre in a weight ratio of 1:99 to 1:9. In the dietary fibre composition the dietary fibre is derived from turmeric, and/or ginger rhizomes. In said composition the dietary fibre is present in an amount of 40% to 95% of the composition by weight.

In some embodiment said composition the insoluble fibre comprises of resistant starch in an amount of 15 to 75% of the composition. The resistant starch comprises unmodified starch of type 1 and type 2, and one or more modified starch selected from a group of type 3 type 4, and type 5.

In some embodiments the said composition is blended with active plant extract, plant nutrients isolated from plants, micro minerals, trace minerals, and vitamins to enhance bioavailability when administered.

In some embodiment said composition is in an oral dosage form. The dosage is in the range of 100 mg to 4000 mg.

Said composition is prepared by heating and then cooling carbohydrate rich plant parts, the plant part is extracted with a non-polar solvent to form a supernatant and de oiled residue, the de oiled residue is treated with acid(s) and after acid treatment the de oiled residue is subjected to enzymatic treatment to obtain the dietary fibre composition.

In yet another embodiment said composition is capable of improving insulin sensitivity, reducing blood glucose level, inhibiting inflammation, for weight loss and reducing colon disorders in mammals.

BRIEF DESCRIPTION OF DRAWINGS

The above and other aspects, features, and advantages of certain exemplary embodiments of the present disclosure will be more apparent from the following description taken in conjunction with the accompanying drawings in which.

DETAILED DESCRIPTION OF THE INVENTION

Figure 1:
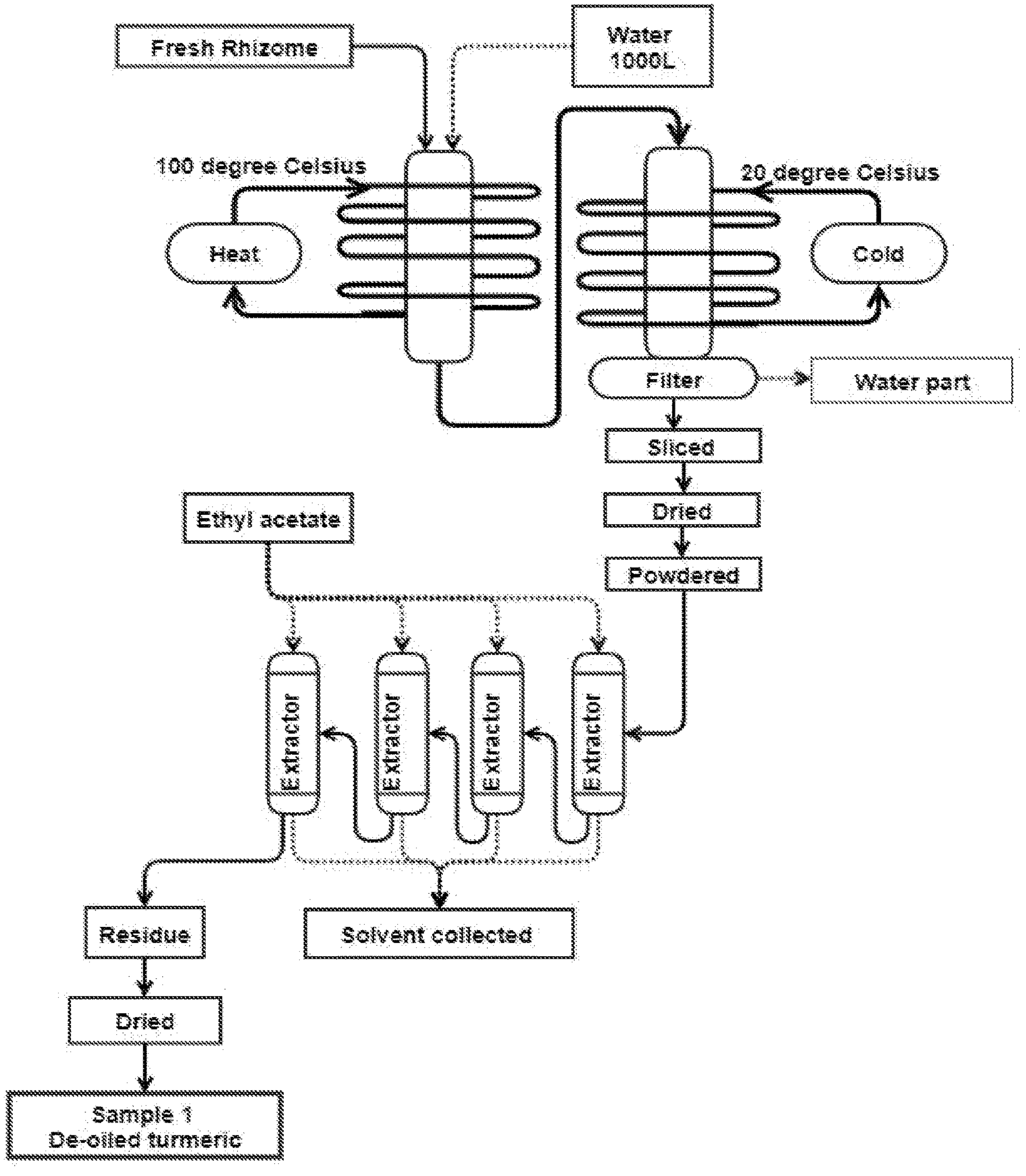
FIG. 1 illustrates a schematic view on turmeric rhizome solvent extraction.
Figure 2:
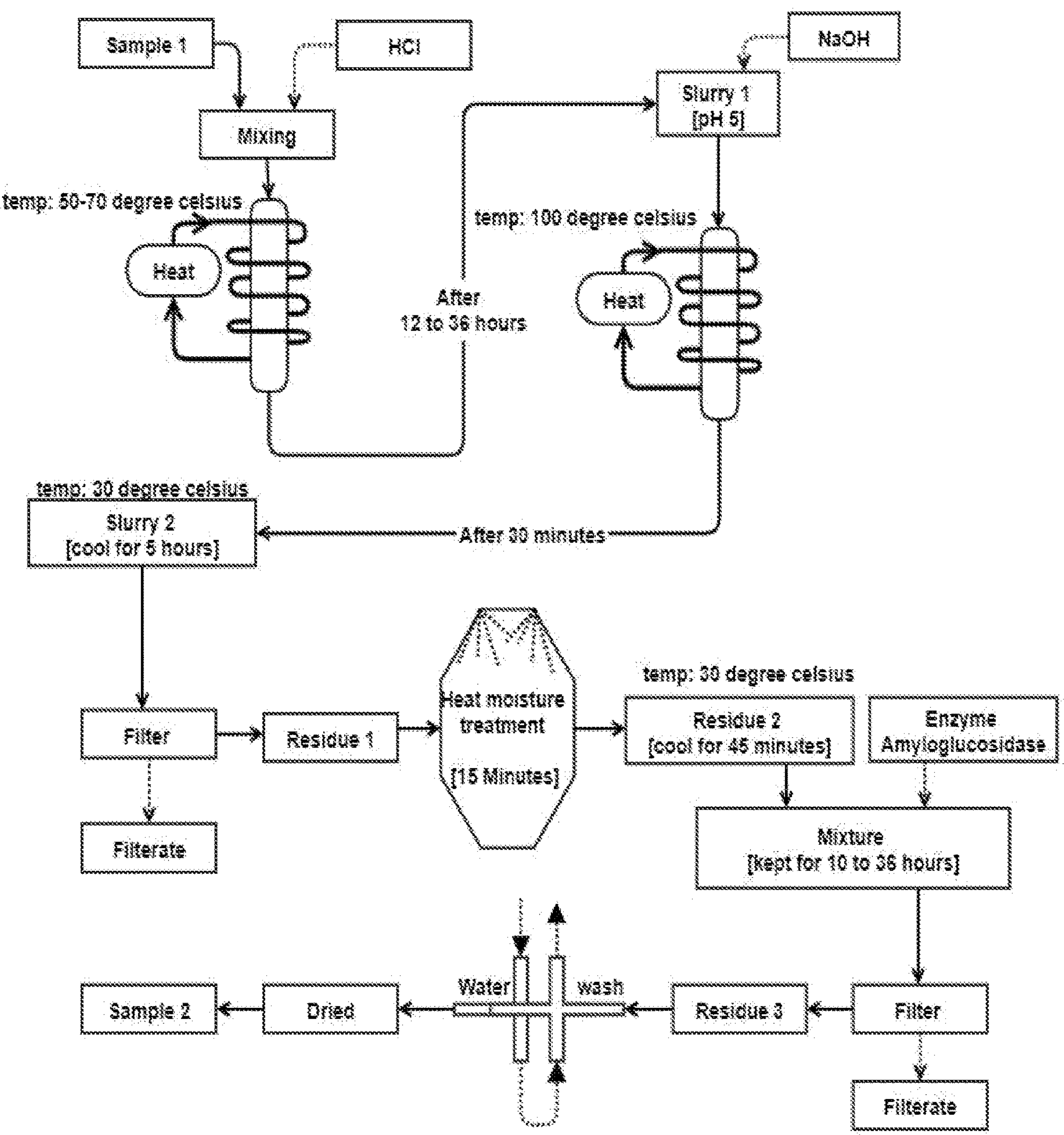
FIG. 2 illustrates a schematic view on preparation of purified resistant starch from a residue obtained from turmeric rhizome solvent extraction.
Figure 3:
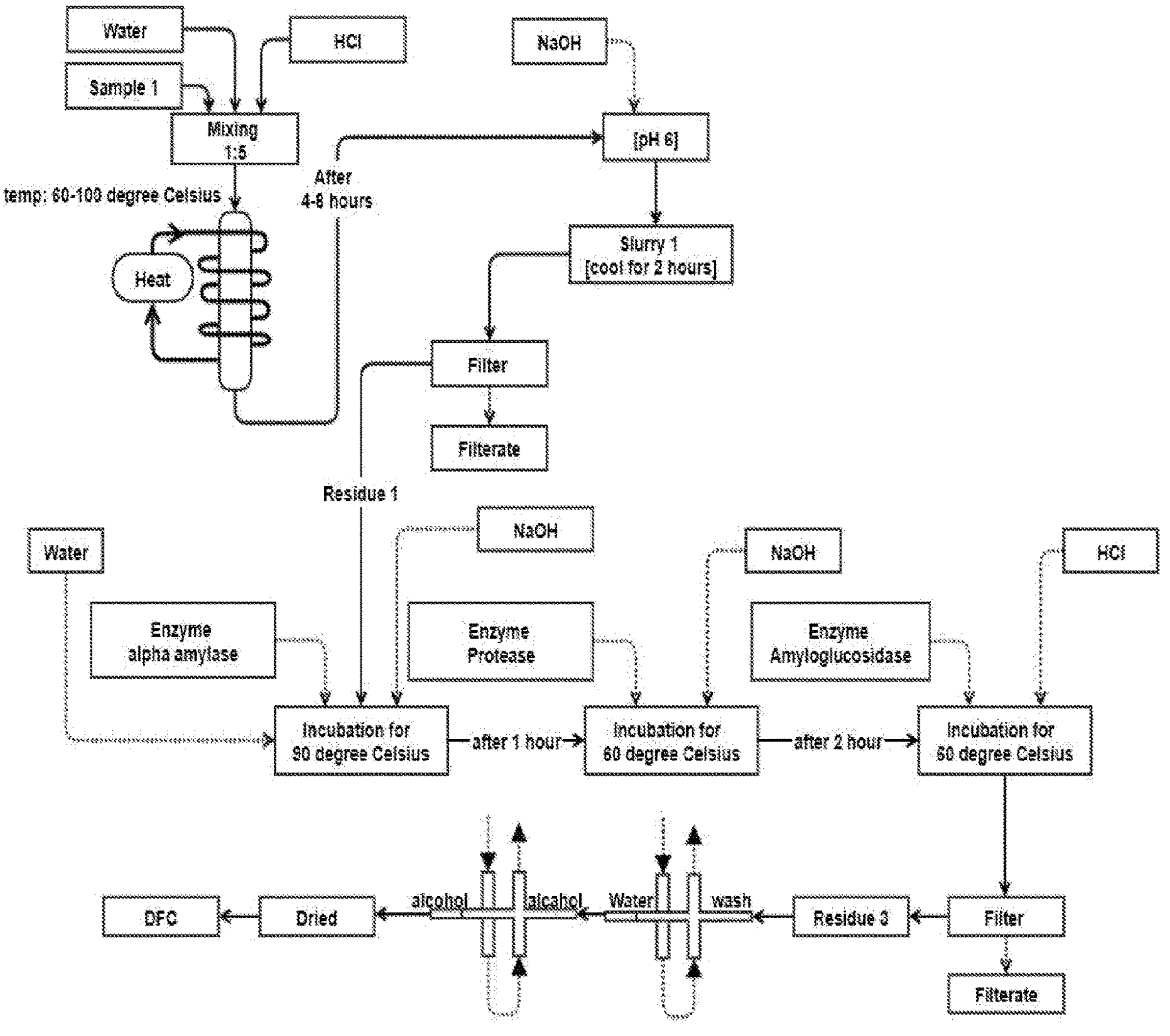
FIG. 3 illustrates a schematic view on preparation of purified dietary fibre composition from a residue obtained from turmeric rhizome solvent extraction.

The following description with reference to the accompanying drawings is provided to assist in a comprehensive understanding of various aspects and embodiments of the disclosure. It includes various specific details to assist in that understanding but these are to be regarded as merely exemplary.

Accordingly, those of ordinary skill in the art will recognize that various changes and modifications of the embodiments described herein can be made without departing from the scope of the disclosure. In addition, descriptions of well-known functions and constructions are omitted for clarity and conciseness.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It is to be understood that all the ratios of blending or blends provided are on weight basis unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself.

Bioavailable curcumin referred to in the description refers to the compositions disclosed in U.S. Pat. No. 7,879,373.

Dietary fibre isthat part of plant material in the diet which is resistant to enzymatic digestion which includes cellulose, noncellulosic polysaccharides such as hemicellulose, pectin substances, gums, mucilages and a non-carbohydrate component lignin. Dietary fibre is also resistant to absorption in the small intestine, with complete or partial fermentation in the large intestine. Dietary fibre is classified as soluble dietary fibre (SDF) and insoluble dietary fibre (IDF). IDFs primarily consist of cellulose, hemicelluloses, resistant starch, and lignin. SDFs include oligosaccharides, including fructooligosaccharide (FOS), pectins, Oglucans (oat and barley grains), galactomannan gums, alginate, and *psyllium.*

Invention relates to a dietary fibre composition (DFC), enzyme resistant starch, derived from natural sources. Sources include but not limited to *Curcuma, Zingiber*, Emblica and other spices. DFC is rich in insoluble dietary fibre, DFC also has an inconsequential amount of soluble fibre. DFC is derived from the de-oiled part of a rhizome or fruit, even the residue (spent) obtained after a solvent extraction of plant parts can be used to manufacture DFC. The plant parts are subjected to heat, chemical and enzyme treatment to produce a DFC with enriched dietary fibre.

Dietary fibre composition means a composition derived from plant parts with 40 to 95% dietary fibre, negligible amount of oil and negligible amount of polyphenols. Dietary fibre composition shall be referred to as 'DFC' or 'fibre' or 'fibre composition' or 'insoluble part of plant' interchangeably throughout the specification if not specified otherwise.

The DFC derived from turmeric comprises insoluble and soluble fibre along with other minor constituents. The insoluble part of turmeric fibre is made up of resistant starch, cellulose, hemicellulose and lignin. The dietary fibre comprises soluble fibre and insoluble fibre, and the weight ratio of soluble fibre to insoluble fibre is in the range of 1:99 to 1:9.

In an embodiment, DFC derived from turmeric rhizome has more than 40% dietary fibre. In an alternative embodiment, DFC has more than 50% dietary fibre. In an alternative embodiment, composition of turmeric has more than 60% dietary fibre. In an alternative embodiment, composition of turmeric has more than 75-80% dietary fibre. In an alternative embodiment, composition of turmeric has about 95% dietary fibre.

In an alternative embodiment the DFC has 40% to 95% dietary fibre. The composition of turmeric also has about 1 to 10% protein, about 5% pectin and rest free starch. In an alternative embodiment the DFC has about 80% to 95% dietary fibre 0%-10% protein, about 5% pectin and rest free starch.

In an alternative embodiment, the DFC derived from turmeric rhizome is standardised with 80% dietary fibre. The composition also contains about 7.2% protein. In an alternative embodiment, the DFC derived from turmeric rhizome is standardised with 80% dietary fibre and ash content below 3.5%. The dietary fibre comprises soluble fibre and insoluble fibre, and the weight ratio of soluble fibre to insoluble fibre is in the range of 1:99 to 1:9. The ash content in each composition DFC is maintained at below 5%.

The high concentrations of resistant starch in DFC from turmeric rhizomes are advantageously produced. The process includes heating and cooling of turmeric rhizome, preferably spent turmeric, for specific time causes reorganization of linear chains of plant starch into a new structure which is resistant to hydrolysis by digestive enzymes. Heating-cooling leads to reorganization of linear chains of starch into a new structure which is resistant to hydrolysis by digestive enzymes. When heating is applied to high-amylose starch, dispersion, disaggregation and breaking of both amylose and amylopectin occur and lead to formation of shorter linear chains. In the next process, cooling down of these chains brings about the formation of double helical aggregates which are denser and more resistant to be hydrolysed. Spent turmeric or spent from any extract referred to in this specification means the de-oiled part left behind after a solvent extraction of the plant part.

When starch undergoes acid treatment it obtains its resistance to digestion by the acid, eroding away the amorphous sections of the starch, leaving behind a higher proportion of crystalline regions relative to what was present prior to acid treatment. These crystalline regions are more difficult for enzymes to access, and as such are more resistant to digestion.

Fresh turmeric rhizomes contain resistant starch in type 1 and 2 forms. The DFC standardised with resistant starch has resistant starch in type 1, 2, 3 and 4 forms (RS1, RS2, RS3 and RS4). RS1 and RS2 are unmodified starch, for the purpose of this application we shall call RS3, RS4 and RS5 modified starch. RS3 is formed by retrograded amylose and amylopectin. RS4 is chemically modified starch. In some embodiment DFC comprises of resistant starch in an amount of 15 to 75% of the composition.

The dietary fibre comprises soluble fibre and insoluble fibre, and the weight ratio of soluble fibre to insoluble fibre is in the range of 1:99 to 1:9. An aspect of the invention is the resistant starch present in DFC, resistant starch comes under the insoluble fibre. In the present application dietary fibre is enriched with at least 15% resistant starch, preferably 15 to 75%. Resistant starch is made up of RS1, RS2, RS3 and RS4.

In an embodiment, the DFC is standardised to 40% to 95% resistant starch. In an alternative embodiment, DFC has more than 40% resistant starch. In an alternative embodiment, DFC has more than 65% resistant starch. In an alternative embodiment, DFC has more than 70% resistant starch. In an alternative embodiment, DFC has more than 75% resistant starch. In an alternative embodiment, DFC has more than 80% resistant starch. In an alternative embodiment, DFC has about 95% resistant starch.

In a preferred embodiment, the DFC standardised with at least 40% resistant starch in which resistant starch is in RS1, RS2, RS3 and RS4 forms. The range ratio of combination of RS1 and RS2, to combination of RS3 and RS4 is 1:0.2 to 1:85.

Resistant starch of type 5 (RS5) is characterized by a lipid component that has complexed with amylose to form a helical structure that contains a fatty acid tail within the central cavity. Lipid components may be but not limited to corn oil, soy lecithin, Caprylic acid, Capric acid, lauric acid, Myristic acid, palmitic acid, stearic acid, oleic acid or linoleic acid. Fatty acid can be prepared by hydrolysing vegetable oils like coconut oil, palm, soybean, sesame oil, rice bran oil, mustard oil, corn oil, groundnut oil, sunflower oil and other edible oils.

In an embodiment, DFC is made with RS5 in it by complexing the starch in DFC with a lipid. The lipid components may be but not limited to corn oil, soy lecithin, Caprylic acid, Capric acid, lauric acid, Myristic acid, palmitic acid, stearic acid, oleic acid or linoleic acid.

Invention discloses a composition derived from natural sources for enhancing the bioavailability and bioactivity of active constituents of turmeric. In an embodiment, bioavailable composition is formed by combining DFC (preferably derived from turmeric rhizome) and curcuminoids. Disclosure also provides a composition where the DFC is blended with curcuminoids additionally containing essential oil or volatile oil of turmeric for enhancing the bioavailability and bioactivity active constituents of turmeric. In alternative embodiment, a bioavailable composition is formed by combining DFC with curcuminoids and essential oil of turmeric.

The curcuminoid mixture or curcuminoids referred in the specification includes curcumin, demethoxycurcumin and bisdemethoxycurcumin. The essential oil of turmeric includes α-turmerone, β-turmerone and ar-turmerone.

In some embodiments of the composition of DFC and curcuminoids enhances bioavailability of constituents such as curcumin, demethoxycurcumin, bisdemethoxycurcumin. In some embodiments of the composition of DFC, curcuminoids and essential oil of turmeric enhances bioavailability of constituent such as curcumin, demethoxycurcumin, bisdemethoxycurcumin, α-turmerone, β-turmerone, and, ar-turmerone. A method of enhancing bioavailability of a constituent in the brain, plasma or serum is provided.

The disclosure provides a method of treatment of brain related disorders by orally administering said composition of DFC and curcuminoids and/or essential oil of turmeric.

Curcuminoids have many known medical benefits at the same time it has poor bioavailability. The composition containing DFC and Curcuminoids can be administered to a human for treating conditions including various cancer, heart diseases, diabetes, rheumatoid arthritis, osteoarthritis, alzheimer's disease, inflammatory bowel diseases, liver fibrosis and cirrhosis, abdominal aortic aneurysms, HIV, pancreatitis, drug-resistant malaria, psoriasis, cystic fibrosis, epilepsy and wound healing. Because of the enhanced bioavailability the potency of the DFC-curcuminoids composition will be much higher than curcuminoid alone.

Methods for treating a central nervous system disorder by administering to a person in need the DFC-curcuminoids composition at an effective dosage. The central nervous system disorders include epilepsy, migraine, Huntington's disease, Alzheimer's disease, depression, Parkinson's disease, Tourette syndrome, dystonia, multiple sclerosis, meningitis, lupus, fibromyalgia, and bipolar disorder. Since the DFC-curcuminoid composition can improve the bioavailability of curcuminoids in the brain the DFC-curcuminoid composition is more potent than curcuminoid mixture alone. In an alternative embodiment the DFC is derived from turmeric rhizome. In an alternative embodiment the DFC is derived from *zingiber* rhizome. In an alternative embodiment the DFC is derived from emblica fruit.

In further embodiment a method to improve the bioavailability of active constituents derived from plants by administering a blend of a plant extract with DFC (40 to 95% dietary fibre). In an alternative embodiment DFC is combined with a plant extract selected from but not limited to turmeric, ginger, amaranth, berberin, black pepper, long pepper, Green tea, Green coffee, Pomegranate, Grape seeds, Emblica, ashwagandha, boswellia and combination thereof to form a DFC-plant composition. In an alternative embodiment the DFC is derived from turmeric rhizome. In an alternative embodiment the DFC is derived from *zingiber* rhizome. In an alternative embodiment the DFC is derived from emblica fruit.

The DFC further comprises micro minerals, trace minerals, and vitamins, wherein the dietary fibre enhances the bioavailability of micro minerals, trace minerals, and vitamins in the mammal body. The DFC further comprises a set wherein the dietary fibre enhances the bioavailability of plant nutrients and the plant nutrients are selected from the group of curcuminoids, withanosides, turmerones, gingerols, Flavone, Quercetin, Genistein, Caffeic Acid, Catechin, Daidzein, Diospyrin, Ellagic Acid, Epicatechin, Etoposide, Ferulic Acid, Geshoidin, Gallic Acid, Pumicalagin, Xanthones, Benzophenones, Hydroxycitric Acid, Anthocyanins, Myristicin, Safrole, Eugenol and combination thereof; wherein the dietary fibre enhances the bioavailability of the plant nutrients in mammal body.

In an embodiment DFC is derived from carbohydrate rich source selected from a group of plants comprising: turmeric, ginger, emblica, rice, wheat, maize, potatoes, cassava, acorns, arrowroot, arracacha, bananas, barley, breadfruit, buckwheat, *canna, colocasia*, katakuri, kudzu, malanga, millet, oats, oca, polynesian arrowroot, sago, sorghum, sweet potatoes, rye, taro, chestnuts, water chestnuts, yams, Amaranth and many kinds of beans, such as favas, lentils, mung beans, peas and chickpeas.

In an alternative embodiment DFC is derived from ginger, a plant from Zingiberaceae family. In an alternative embodiment DFC is derived from Emblica *officinalis*. In alternative embodiment the composition is derived from spices.

The DFC has a place in novel food products, for food processing purposes, as functional food, dietary supplementation purposes and pharmaceutical preparations. The term "dietary supplement" refers to a preparation or a formulation comprising an effective amount of composition from turmeric used to supplement the diet of an animal or human to provide therapeutic, preventive and/or beneficial effects. The term "pharmaceutical preparations" refers to a preparation comprising an effective amount of DFC formulated for therapeutic use.

The term "functional foods" refers to food substances, fresh or processed, comprising composition from turmeric that provide health-promoting and/or disease-preventing benefits beyond the basic nutritional function of supplying nutrients. The composition of the present invention in the form of functional foods further comprises at least one edible ingredient.

As functional foods, dietary supplement, or pharmaceutical preparation, the DFC may be provided as, but not limited to, juices, fruit drinks, carbonated beverages, milk, nutritional drinks, ice cream, breakfast cereals, biscuits, cakes, muffins, cookies, candies, bread, toppings, bread, fibre bars, soups, crackers, baby formulae, teas, salad dressings, cooking oils, cheese, butter, jellies, jams or preserves. Further, at least one edible ingredient in the functional food compositions may be any suitable carrier or edible additive. "Edible ingredient" or "edible additive" according to the present invention includes, but are not limited to, acidulants, antioxidants, sequestrants, colours, colour retention agent, sweeteners, emulsifiers, fats, oils, flavours, flavour enhancers, flour, flour treatment agents, gums, preservatives, stabilizers, spices, thickeners, bulking agents, vitamins, anticaking agents, antifoaming agents or humectants.

Yet another aspect of the invention is the use of the DFC derived from the turmeric for reducing abdominal fat, reducing blood glucose level, for weight loss and improving insulin sensitivity. Said DFC functions as a prebiotic and can be fermented in the colon to yield products beneficial to the host, such as short-chain fatty acids, which plays a significant role in prevention of colorectal cancer. DFC contributes to faecal bulking, shortens intestinal transit time of food bolus, and reduces development of cancerous lesions of the bowel in animal models. DFC is effective for controlling lipid metabolism.

The DFC and other compositions of DFC as disclosed above when used in the form of pharmaceutical preparations or dietary supplement comprises in addition to DFC, at least one pharmaceutically acceptable excipient.

At least one pharmaceutically acceptable excipient present in the pharmaceutical preparations or dietary supplements with DFC includes, but is not limited to, fillers, binders, glidants, lubricants, stabilizers, solubilizers, disintegrants, polymers, sweeteners or flavourants. Fillers employed in the DFC include, but are not limited to, lactose monohydrate, microcrystalline cellulose or dicalcium phosphate. Binders employed in the compositions of the present invention include, but are not limited to, starch, pregelatinized starch, polyvinyl pyrrolidine (PVP), copovidone, cellulose derivatives, such as hydroxypropylmethyl cellulose (HPMC), hydroxypropyl cellulose (HPC) and carboxymethylcellulose (CMC) and their salts or like. Glidants employed include, but are not limited to, colloidal silicon dioxide, magnesium trisilicate, powdered cellulose, talc, tribasic calcium phosphate and the like. Lubricants employed in the DFC include, but are not limited to, colloidal silica, magnesium stearate, hydrogenated vegetable oils and triglycerides of stearic acid, palmitic acid or the like. The compositions of the present invention include at least one disintegrant such as, but not limited to, natural, modified or pregelatinized starch, crospovidone, croscarmellose sodium, sodium starch glycolate, low-substituted hydroxypropyl cellulose as well as effervescent disintegrating systems. The solubilizer includes, but is not limited to, hydrophilic surfactants or lipophilic surfactants or mixtures thereof. The surfactants may be anionic, non-ionic, cationic, and zwitterionic surfactants. Examples of solubilizers include, but are not limited to cetostearyl alcohol, cholesterol, diethanolamine, ethyl oleate, ethylene glycol palmitostearate, glycerin, glyceryl monostearate, isopropyl myristate, lecithin, medium-chain glyceride, monoethanolamine, oleic acid, propylene glycol, polyoxyethylene alkyl ether, polyoxyethylene castor oil glycoside, polyethylene sorbitan fatty acid ester, polyoxyethylene stearate, propylene glycolalginate, sorbitan fatty acid ester, stearic acid, sunflower oil, triethanolmine, cyclodextrins and mixtures thereof. Examples of surfactants include, but are not limited to, sodium docusate, glyceryl monooleate, polyethylene alkyl ether, polyoxyethylene sorbitan fatty acid ester, sodium lauryl sulphate, sorbic acid, sorbitan fatty acid ester, and mixtures thereof. The tablet compositions of DFC may also include stabilizers such as, but not limited to, benzoic acid, sodium benzoate, citric acid, and the like. Polymers employed in the compositions of the DFC include, but are not limited to, cellulose derivatives; polyhydric alcohols; saccharides, gums and derivatives thereof; vinyl derivatives, polymers, copolymers or mixtures thereof; maleic acid copolymers; polyalkylene oxides or copolymers thereof; acrylic acid polymers and acrylic acid derivatives; or any combinations thereof. Sweeteners employed in the compositions include, but not limited to, aspartame, *stevia* extract, *glycyrrhiza*, saccharine, saccharin sodium, acesulfame, sucralose and dipotassium glycyrrhizinate. Flavourants employed in the compositions include, but not limited to, mint flavour, orange flavour, lemon flavours, strawberry aroma, vanilla flavour, raspberry aroma, cherry flavour, tutti-frutti flavour, magnasweet 135, key lime flavour, grape flavour, and fruit extracts.

Further, the DFC is used as a coating material in combination with other known coating materials. Pharmaceutical preparations can be provided in the form of, but not limited to, tablets, capsules, emulsions, suspensions, powders, pellets or granules for oral administration.

Disclosure provides a DFC prepared by a method including boiling fresh plant parts in water followed by cooling. Boiled plant parts are dried and powdered. The powdered plant parts are extracted with solvent. Solvents for this purpose include acetone, hexane, ethyl acetate, dicholoroethane, chloroform. The residue is dried to obtain de-oiled residue. Dried de oiled residue is subjected to chemical modification followed by enzyme treatment to form dietary fibre composition. Preferred plant parts are carbohydrate rich part of plants selected from a group of rice, wheat, maize, potatoes, cassava, acorns, arrowroot, arracacha, bananas, barley, breadfruit, buckwheat, canna, colocasia, katakuri, kudzu, malanga, millet, oats, oca, polynesian arrowroot, sago, sorghum, sweet potatoes, rye, taro, chestnuts, water chestnuts, yams, Amaranth, turmeric, ginger, emblica and many kinds of beans, such as favas, lentils, mung beans, peas, chickpeas and combination thereof.

In an alternative embodiment DFC derived from turmeric or ginger rhizome is prepared by a method including the step of boiling fresh rhizomes of turmeric in water followed by cooling. Next step the boiled rhizomes are dried and powdered. In the next step the powdered turmeric rhizome is extracted with solvent, preferably a non-polar solvent. Solvents for this purpose include acetone, hexane, ethyl acetate, dicholoroethane, chloroform, etc. In the next step the residue left after the solvent extraction is dried and powdered to get de-oiled turmeric. In the next step dried de oiled turmeric is subjected to chemical modification followed by enzyme treatment to form dietary fibre composition. Rhizomes can be de-oiled by steam distillation also. The spent obtained from curcumin extraction, the residue left after curcuminoids and oil is extracted from turmeric rhizome, that spent residue can be used for producing DFA.

In one preferred embodiment method of preparing resistant starch rich DFC from turmeric is provided. Boiling fresh rhizomes of turmeric in water for 2 hours at 100° C. and followed by cooling. Separate the rhizomes from the water part. Rhizomes are extracted with ethyl acetate to obtain ethyl acetate extract and a first residue. The first residue is separated from ethyl acetate. First residue is kept in HCl at 50° C. to 70° C. incubation for 12 to 36 hours to form the first slurry. The pH of the first slurry is adjusted about 5 by adding NaOH. The first slurry is kept at 100° C. incubation for 30 minutes. After the incubation the first slurry is cooled at room temperature for 5 hours. The first slurry is filtered to obtain a second residue. The second residue is moistened with steam. The second residue is cooled to room temperature to form a third residue. Enzyme amyloglucosidase is added to the third residue and kept for 10 to 36 hours to form a second slurry. Filter out the second slurry to obtain fourth residue. Fourth residue is washed with water and dried to obtain the dietary fibre composition with 75±5% resistant starch.

In one preferred embodiment method of preparing DFC from turmeric is provided. Boil fresh rhizomes of turmeric in water for 2 hrs at 100° C. and followed by cooling. Separate the water part. Boiled rhizomes are sliced, dried and powdered. The powdered turmeric rhizome is extracted with ethyl acetate to obtain ethyl acetate extract and a residue. Residue is separated from the ethyl acetate extract and solvent is removed from the residue. The residue is dried to obtain de-oiled turmeric and it shall be referred to as sample 1. Sample 1 has about 30 to 50% dietary fibre and about 15 to 25% resistant starch. Resistant starch is part of dietary fibre or one of the dietary fibre. Sample 1 is mixed with water and kept at pH 1.5 by adding HCl for 4-8 hours at 60-100° C. to form slurry. After incubation pH of slurry is adjusted to 6 by adding NaOH to form slurry. Slurry is cooled to room temperature for 0.5-2 hours. Filtered, washed with water, and wet residue is obtained. The residue has 50 to 60% dietary fibre. Residue is mixed with water and pH is maintained at 6 by adding NaOH. Enzyme alpha amylase is added and kept for 1 hour at 80-110° C. Cooled and adjusted pH to 7.4 by adding NaOH. After this step dietary fibre is enriched up to 65±5%. Enzyme protease is added and kept at 60° C. for 0.5-2 hours. Cooled to room temperature and maintained pH at 4.5 by adding 10% HCl, after this step the dietary fibre is enriched up to 72±5%. Amyloglucosidase is added and kept at 60° C. for 0.5-2 hours. Cooled at room temperature to form slurry. Slurry is filtered and residue is washed 3 times with water and 2 times with alcohol. Residue is dried at 60° C. under vacuum and powdered to form powder of dietary fibre composition of turmeric with 80±5% dietary fibre.

In one embodiment, the method of preparing the DFC from turmeric includes boiling fresh rhizomes of turmeric in water followed by cooling. Boiled rhizomes are dried and powdered. The powdered turmeric rhizome is extracted with a solvent. The solvents for this purpose are selected from a group of but not limited to acetone, hexane, ethyl acetate, dicholoroethane, chloroform and a combination thereof. The solvent part is removed and the residue is dried to obtain de oiled turmeric. Further the dried de oiled turmeric is subjected to chemical modification followed by enzyme treatment to form resistant starch composition. In an alternative embodiment the dried powdered turmeric is further boiled and cooled in water before deoiling with a solvent. In an alternative embodiment the de-oiled turmeric is further boiled and cooled in water before chemical treatment.

The Chemical modifications include but are not limited to acetic anhydride, chloroacetic acid, citric acid, succinic acid, hydrochloric acid treatment. In one embodiment, de-oiled turmeric is subjected to HCl treatment. In an alternative embodiment, de-oiled turmeric is subjected to citric acid treatment. In an alternative embodiment de-oiled turmeric is subjected to succinic acid treatment. In an alternative embodiment de-oiled turmeric is subjected to acetic anhydride treatment. In an alternative embodiment, de-oiled turmeric is subjected to acetic chloroacetic acid treatment. In an alternative embodiment de-oiled turmeric is subjected to acid treatment from one or more acids selected from the group of acetic anhydride, chloroacetic acid, citric acid, succinic acid, hydrochloric acid. Acid treated turmeric then undergoes enzyme treatment to form high resistant starch rich DFC.

The enzymatic treatment include treating the residue from the acid treatment with one or more enzyme selected from a group of protease, α-amylase, β-amylase, glucoamylase, pullulanase, pancreatin, isoamylase, amyloglucosidase and combination thereof.

Enzyme treated turmeric is subjected to lipid treatment using citric acid and palmetic acid followed by enzyme treatment using enzymes alpha amylase and amyloglucosidase to form powder of dietary fibre composition of turmeric.

In another embodiment, fresh rhizomes of turmeric are boiled in water for 2 hrs at 100° C. and followed by cooling. Separate the water part. Boiled rhizomes are sliced, dried and powdered. The powdered turmeric rhizome is extracted with ethyl acetate to obtain ethyl acetate extract and a residue. Residue is separated from the ethyl acetate extract and solvent is removed from the residue. The residue is dried to obtain de-oiled turmeric and it shall be referred to as sample 1.

Sample 1 is treated with water and moistened with steam. Cooled to room temperature and kept for 2 hours. After 2 hours, 5% HCl is added to sample 1, stirred at 60° C. for 8 hours and cooled.

Water is added to acid treated sample 1 and adjusted the pH to 4.5 by adding 1N NaOH. Enzyme pullulanase is added and kept at 60° C. for 2 hours to form slurry 1.

2-5% citric acid and 5-12% palmetic acid is added to slurry 1 and kept at 80° C. for 2 hours. Cooled at room temperature to form slurry 2. pH of slurry 2 is maintained at 7.4 by adding 1N NaOH. Enzyme protease is added to slurry 2 and kept at 60° C. for 30 minutes form slurry 3. pH of slurry 3 is maintained at 6 by adding 1N HCl. Enzyme alpha amylase and amyloglucosidase were added to slurry 3 and kept at 60° C. for 4 hrs. Cooled at room temperature to form slurry 4. Slurry 4 is filtered and residue is washed 3 times with water and 2 times with alcohol. Residue is dried at 60° C. under vacuum and powdered to form powder of dietary fiber composition of turmeric.

Another aspect of the invention is a composition made by combining DFC with 40 to 95% turmeric fibre, with curcuminoids and/or essential oil of turmeric. In an embodiment a composition is formed by combining the DFC with curcuminoids in 1:99 to 99:1 ratio. In an alternative embodiment the ratio between the DFC to curcuminoids is 1:1.

In an alternative embodiment a composition is formed by combining the DFC with essential oil of turmeric in 1:99 to 99:1 ratio. In an alternative embodiment the ratio between the DFC to essential oil of turmeric is 1:1. In an alternative embodiment the ratio between the DFC to essential oil of turmeric is 10:1. In an alternative embodiment the ratio between the DFC to essential oil of turmeric is 5:1.

In an alternative embodiment a composition is formed by combining the DFC with essential oil of turmeric and curcuminoids where DFC to curcuminoids is in 1:99 to 99:1 and DFC to essential oil of turmeric is in 1:99 to 99:1. In an alternative embodiment DFC to curcuminoids to essential oil of turmeric is in 1:1:1 weight ratio. In an alternative embodiment DFC to curcuminoids to essential oil of turmeric is in 10:10:1 to 12:12:1 weight ratio.

Any turmeric extract rich in curcuminoids can be used for the DFC-curcuminoid composition. In the present application curcuminoids mixture, active curcuminoid composition and essential oil of turmeric are made by the method disclosed in U.S. Pat. Nos. 7,879,373, 8,153,172, 8,993,013 or 8,623,431.

Methods of preparing compositions of DFC, curcuminoid and/or essential oil are disclosed. In one embodiment the method includes suspending a powdered extract of curcuminoid mixture and DFC in water to form a suspension. The suspension is concentrated to form a slurry, and water is stripped from the slurry to obtain a powder composition of DFC, and curcuminoid.

In an alternative embodiment the method includes suspending DFC in water to form a suspension. Essential oil of turmeric is added to the suspension to form a mixture. Mixture is concentrated and pulverised to form a slurry, and water is stripped from the slurry to obtain a powder composition of DFC, and essential oil of turmeric.

In an alternative embodiment the method includes suspending curcuminoid mixture and DFC in water to form a suspension. Essential oil of turmeric is added to the suspension to form a mixture. Mixture is concentrated and pulverised to form a slurry, and water is stripped from the slurry to obtain a powder composition of DFC, curcuminoid and essential oil of turmeric.

In another embodiment, the method of preparation of the composition containing curcuminoid and/or essential oil of turmeric with DFC includes mixing curcuminoid and/or essential oil with DFC by a simple blending process.

Another aspect of the combination of DFC with curcuminoids and/or essential oil of turmeric is the enhancement in the bioavailability curcuminoids and turmerone in the body, especially the enhancement in the bioavailability of curcumin, demethoxycurcumin, bisdemethoxycurcumin in tissues, plasma or serum. Curcumin, demethoxycurcumin, bisdemethoxycurcumin makes up about 90 to 95% of the curcuminoids or curcuminoids mixture. Turmerone makes up most of the essential oil of curcumin. The tissues include Heart, Kidney, Brain, Liver, Pancreas, Lungs, Intestine, Stomach and Skin.

One study conducted on rats showed availability of active constituents in the brain when combined with DFC. Result showed animals fed with composition of DFC and bioavailable turmeric formulation showed high detection of curcumin, demethoxycurcumin, bisdemethoxycurcumin, α-Turmerone, β-turmerone and Ar-turmerone in brain. In the curcuminoid alone group, small detection of curcumin is found. Demethoxycurcumin and bisdemethoxy curcumin are not detected in brain of rats fed with curcuminoids alone. Whereas animals fed with composition containing DFC and curcuminoid alone enhance the availability of curcumin, demethoxy curcumin and bisdemethoxycurcumin in the rat brain compared to curcuminoid alone group. Curcuminoids in combination with DFC have 16-fold higher bioavailability compared to regular curcuminoids.

In one embodiment, a method to increase bioavailability of curcuminoids in tissue, plasma and serum by administering the composition containing DFC and curcuminoids, the composition enhances bioavailability of constituents in plasma, tissues and serum compared to curcuminoids per se. In an alternative embodiment a method to increase bioavailability of curcuminoids in brain by administering the composition containing DFC and curcuminoids, the composition enhances bioavailability of constituents in brain compared to curcuminoids per se.

In one embodiment, a method to increase bioavailability of curcuminoids and turmerone in tissue, plasma and serum by administering the composition containing DFC and curcuminoids and/or essential oil of turmeric, the composition enhances bioavailability of constituents in plasma, tissues and serum compared to curcuminoids and/or essential oil per se. In an alternative embodiment a method to increase bioavailability of curcuminoids and turmerone in brain by administering the composition containing DFC and curcuminoids and/or essential oil of turmeric, the composition enhances bioavailability of constituents and turmerones in brain compared to curcuminoids per se.

Anti-Inflammatory Activity, Anti-Diabetic Activity of DFC:

Another aspect of the invention is the anti-inflammatory activity of the DFC is noted by using the Wistar rat model. Results showed that animals treated with DFC standardised with 80% dietary fibre showed 61% inhibition of inflammation compared to animals treated with standard Diclofenac drug. Animals treated with soluble dietary fibre from Guar beans at the same dosage showed 46% inhibition of inflammation and animals treated with modified starch from tapioca showed only 40% inhibition of inflammation.

In an embodiment, a method to reduce inflammation in a mammal in need thereof by administering to the mammal an effective dose of DFC with 40 to 95% dietary fibre. In an alternative embodiment the effective dosage ranges from 100 mg to 4000 mg per day for humans. In an alternative embodiment the effective dosage ranges from 10 to 200 mg for medium and small size mammals.

Another aspect of the invention is the anti-diabetic activity of the DFC. Glucose tolerance study of turmeric dietary fibre is conducted in normal Sprague dawley rats. Results showed that animals fed with turmeric fibre (80% dietary fibre) showed a 77% inhibition in rise in blood glucose level compared to rats fed with soluble dietary fibre from Guar beans, which showed only 59% inhibition in rise in blood glucose level. Animals fed with modified starch from Tapioca showed 56% inhibition in rise in blood glucose level.

In an embodiment, a method to inhibit rise in blood sugar in a mammal in need thereof by administering to the mammal an effective dose of DFC with 40 to 95% dietary fibre. In an alternative embodiment the effective dosage ranges from 100 mg to 4000 mg per day for humans. In an alternative embodiment the effective dosage ranges from 10 to 200 mg for medium and small size mammals.

In another embodiment the composition of DFC with curcuminoids and/or essential oil of turmeric is made into a dosage form such as capsule, tablet, mini tablet, granule, sachet, powder, paste, infusion, ampoule, solution, suspension, emulsion, pills, cream, enteric coated formulations. Oral dosage forms of the compositions are disclosed. In an alternative embodiment the DFC makes up about 1 to 50% of an oral dosage form of 100 to 4000 mg.

In an alternative embodiment, the composition containing DFC with curcuminoids and/or essential oil of turmeric is blended with excipients selected from the group of but not limited to a disintegrant, diluents, binders, fillers, a carrier, adsorbents, emulsifiers, lubricants, stabilizing agents, anti-adherents, galidants, antioxidants and mixtures thereof.

Resistant starch in the composition is analysed by AOAC official method 2002.02. Non-resistant starch is solubilized and hydrolyzed to glucose by the combined action of pancreatic alpha amylase and amyloglucosidase (AMG) for 16 h at 37° C. The reaction is terminated by addition of ethanol or industrial methylated spirits (IMS) and RS is recovered as a pellet by centrifugation. RS in the pellet is dissolved in 2M KOH by vigorously stirring in an ice-water bath. This solution is neutralized with acetate buffer and the starch is quantitatively hydrolyzed to glucose with AMG. Glucose is measured with glucoseoxidase-peroxidase reagent (GOPOD), which is a measure of RS content.

Dietary fiber in the composition is analysed by AOAC-991.43. Samples are gelatinized with a heat-stable alpha amylase and then enzymatically digested sequentially with protease and amyloglucosidase to remove protein and starch.

For total dietary fibre (TDF) enzyme digestate is treated with alcohol to precipitate soluble dietary fibre before filtering and TDF residue is washed with alcohol and acetone, dried and weighed. TDF residues are corrected for protein, ash and blank.

For Insoluble dietary fibre (IDF) and soluble dietary fibre (SDF) determination, enzyme digestate is filtered, and then residue is washed with warm distilled water dried, and weighed. Combined solution of filtrate and water washings are precipitated with 4 volumes of 95% ethanol (EtOH) for soluble dietary fibre (SDF) determination. Precipitate is then filtered and dried. Both SDF and IDF residues are corrected for protein, ash and blank. Total dietary fibre=IDF+SDF The most common enzymes for starch modification include α-amylase, β-amylase, glucoamylase, pullulanase, pancreatinand isoamylase, amyloglucosidase. Amyloglucosidase (AMG, glucan 1,4-α-glucosidase) is an exo-acting member of the α-amylase family of starch-hydrolyzing enzymes. AMG enzymes action the non-reducing ends of starch and oligosaccharide molecules to yield glucose and low molecular weight dextrins.

EXAMPLES

The following illustrate the manner and process of making the invention through following working examples, they do not limit the scope of the invention in any ways, rather they are for the purpose of understanding the invention only. The examples are descriptive enough in such full, clear, concise, and exact terms as to enable any person skilled in the art to which it pertains. However, the disclosure is not limited to the Examples.

Example 1

Method of Extracting, Modifying and Enriching Resistant Starch

This method could be used to extract resistant starch from ginger rhizome, emblica fruit and other similar plant parts.

About 500 kg of fresh rhizomes of turmeric were collected. Fresh rhizomes were boiled in 1000 L of water for 2 hrs at 100° C. Boiled rhizomes were cooled at 20° C. After cooling, boiled rhizomes and water parts were separated. Boiled rhizomes were sliced and dried. Dried rhizomes were powdered to obtain 100 kg powdered turmeric rhizome. The powdered turmeric rhizome was extracted with 600 litres of ethyl acetate. The extraction was carried out at 78° C. temperature for 1 hr. After initial extraction, the extraction process was repeated 3 more times using 600 L ethyl acetate for each extraction to obtain ethyl acetate extract and first residue. First residue was separated from the ethyl acetate extract. Solvent was removed from the residue and dried to form 90 kg dried de-oiled turmeric (sample 1). Sample 1 contains 20% resistant starch and about 40% dietary fibre.

Sample 1 was kept at HCl for 12-36 hours at 50° C. to 70° C. to form a slurry. After incubation pH of slurry was adjusted to 5 by adding NaOH to form slurry 1. Resistant starch in the slurry was 40%.

Heated to 100° C. for 30 minutes and cooled to room temperature for 5 hours. Filtered and residue 2 was obtained. Residue 2 contains 44% resistant starch.

Residue 2 was moistened with steam for 15 minutes. Cooled to room temperature for 45 minutes to form residue 3. Residue 3 contains 50% resistant starch.

Enzyme amyloglucosidase was added (10 ml per Kg, 450 GU/gm, Advanced Enzymes) to residue 3 and kept for 10 to 36 hours to form slurry 2. Filtered and residue 4 was formed. Residue 4 was washed with water and dried to form 40 kg of sample 2.

Sample 2 was light yellow in colour with 75% resistant starch.

Method of Analysis of Resistant Starch a) Hydrolysis of nonresistant starch—accurately weighed 100 mg sample and 4.0 mL pancreatic α-amylase (10 mg/mL) containing amyloglucosidase (3 U/mL) was added. Mix on a vortex mixer and incubate at 37° C. with continuous shaking for 16 h. 4.0 mL methylated spirit was added, mixed the contents vigorously on a Vortex mixer and centrifuged for 10 minutes. Decanted the supernatant and re-suspended the residue in 2 mL 50% methylated spirit with vigorous mixing in a vortex mixer. 6 mL 50% methylated spirit was added, mixed and centrifuged again for 10 minutes. Decanted supernatants and residue was collected.

(b) Measurement of RS—2 mL 2M KOH was added to the residue and stirred for 20 minutes in an ice-water bath over a magnetic stirrer. 8 mL 1.2M sodium acetate buffer (pH 3.8) was added with stirring. Immediately added 0.1 mL amyloglucosidase (3300 U/mL), mixed well, and then kept in a water bath at 50° C. Incubated for 30 minutes with intermittent mixing on a Vortex mixer and centrifuged. Supernatant and residues were separated. Residue was made up to 100 mL using water. To 0.1 mL of solution, 3.0 mL GOPOD (glucose oxidase-peroxidase reagent) reagent was added and mixed on a Vortex mixer. A blank was prepared by mixing 0.1 mL 0.1M sodium acetate buffer (pH 4.5) and 3.0 mL GOPOD reagent. Incubated at 50° C. for 20 min and cooled. Absorbance of each solution was measured at 510 nm.

$$RS(g/100\ g\ \text{sample}) = A \times F \times (100/0.1) \times (1/1000) \times (100/W) \times (162/180)$$

$$= A \times F/W \times 90$$

Where A=averaged absorbance read against the reagent blank;

F=conversion factor from absorbance to micrograms

100/0.1=volume adjustment;

1/1000=conversion from micrograms to milligrams;

W=weight of test portion analyzed;

100/W=factor to present starch as a percentage of test portion weight;

162/180=factor to convert from free glucose, as determined, to anhydro-glucose as occurs in starch.

Example 2

Method of Extracting and Enriching Dietary Fibre from Rhizome 500 kg of fresh rhizomes of turmeric were collected. Fresh rhizomes were boiled in 1000 L of water for 2 hrs at 100° C. Boiled rhizomes were cooled at 20° C. After cooling, boiled rhizomes and water parts were separated. Boiled rhizomes were sliced and dried. Dried rhizomes were powdered to obtain 100 kg powdered turmeric rhizome. The powdered turmeric rhizome was extracted with 600 litres of ethyl acetate. The extraction was carried out at 78° C. temperature for 1 hr. After initial extraction, the extraction process was repeated 3 more times using 600 L ethyl acetate for each extraction to obtain ethyl acetate extract and a residue. Residue was separated from the ethyl acetate extract. Solvent was removed from the residue and dried to form 90 kg dried de-oiled turmeric (sample 1).

Sample 1 was mixed with 360 L water and kept at pH 1.5 by adding 50% HCl for 4-8 hrs at 60° C. to form slurry 1. After incubation pH of slurry was adjusted to 6 by adding 10% NaOH to form slurry 2. Slurry 2 was cooled to room temperature for 2 hours. Filtered, washed with water and wet residue 1 was obtained.

Residue 1 was mixed with 150 L water and pH was maintained at 6 by adding 1N NaOH. Enzyme alpha amylase (10 ml/Kg, 80000 U/ml) was added and kept for 1 hr at 90° C. Cooled and adjusted pH to 7.4 by adding 10% NaOH. Enzyme protease (1 ml/Kg, 100,000 U/ml) was added and kept at 60° C. for 2 h. Cooled to room temperature and maintained pH at 4.5 by adding 10% HCl. Amyloglucosidase (10 ml/Kg, 2500 U/ml) was added and kept at 60° C. for 2 hrs. Cooled at room temperature to form slurry 3.

Slurry 3 was filtered and residue 2 was washed 3 times with water and 2 times with alcohol. Residue was dried at 60° C. under vacuum and powdered to form powder of dietary fibre composition of turmeric (product 1).

Dietary fibre content in the powder of turmeric fibre composition was found to be 80%.

Method of Analysis of Dietary Fibre (AOAC-991.43)

Samples were gelatinized with a heat-stable alpha amylase (pH 6, 100° C., 30 min) and then enzymatically digested sequentially with protease (pH 7.5, 60° C., 30 min) and amyloglucosidase (pH 6, 0° C., 30 min) to remove protein and starch.

For total dietary fibre (TDF) enzyme digestate was treated with alcohol to precipitate soluble dietary fibre before filtering and TDF residue was washed with alcohol and acetone, dried and weighed. TDF residues were corrected for protein, ash and blank.

For Insoluble dietary fibre (IDF) and soluble dietary fibre (SDF) determination, enzyme digestate was filtered, and then residue was washed with warm distilled water dried, and weighed. Combined solution of filtrate and water washings were precipitated with 4 volumes of 95% ethanol (EtOH) for soluble dietary fibre (SDF) determination. Precipitate was then filtered and dried. Both SDF and IDF residues were corrected for protein, ash and blank.

$$\text{Total dietary fibre}=IDF+SDF$$

AOAC official method 991.43 for total dietary fibre (TDF) is often used for measuring Enzyme Resistant starch also. In this method Resistant Starch is the difference between the initial dry weight of the sample and the weight of the sample after hydrolysis, rinsing, and drying (Megazyme 2012).

$$\text{Enzyme resistant Starch (\%)}=[\text{Insoluble Residue weight } (g)/\text{sample weight } (g)]\times 100$$

Example 3

Method of Preparation of Combination of Turmeric Fibre and Curcuminoids

About 100 g of Product 1 prepared as per example 2 was taken, it was blended with about 100 g curcuminoids with 95% purity in 1:1 weight ratio in a mixing vessel and churned till the blend became uniform.

Example 4

Method of preparation of combination of turmeric fibre and curcuminoids with essential oil of turmeric.

Suspending about 100 g of powdered curcuminoid with 95% purity in water. Since it is insoluble in water it stays suspended. About 100 g Product 1 prepared as per example 2 was added to form a suspension followed by 10 g of Essential oil of turmeric was added to the suspension to obtain a mixture. The mixture was concentrated and pulverized to obtain slurry. Water was stripped from the slurry to obtain a powder of the composition having DFC, curcuminoid mixture and essential oil of turmeric.

Example 5

Anti-Diabetic Study

Glucose tolerance study of turmeric dietary fibre was conducted in normal Sprague dawley rats. After the acclimatization period, rats were divided into four groups (Table 1). The animals were fasted overnight and fasting blood glucose (FBG) was recorded using glucometer. After FBG determination, the animals were fed orally with respective test samples or vehicles. After 30 minutes of a test sample, glucose (2.5 g/kg) was orally fed to the animals. The blood glucose level was again determined for all the animals at 30 min, 1 h, 2 h and 3 h after glucose feeding. The difference in blood glucose level from respective FBG was calculated for all the rats and compared with control.

TABLE 1

Animals grouping and treatment for glucose tolerance test.

| Groups | Treatment |
|---|---|
| Group 1 | Vehicle (0.5% polysorbate 80) + Glucose (2.5 g/kg) |
| Group 2 | Turmeric dietary fibre (80%) (50 mg/kg/day) + Glucose (2.5 g/kg) |
| Group 3 | Soluble dietary fibre from Guar beans (50 mg/kg/day) + Glucose (2.5 g/kg) |
| Group 4 | Modified starch from Tapioca (50 mg/kg/day) + Glucose (2.5 g/kg) |

TABLE 2

Blood glucose level and percentage inhibition of rise in blood glucose in animals.

| | Blood glucose level | | | | | Percentage inhibition of rise in blood glucose | | | | Average % |
|---|---|---|---|---|---|---|---|---|---|---|
| | FBS | 30 min | 1 Hr | 2 Hr | 3 Hr | 30 min | 1 Hr | 2 Hr | 3 Hr | Inhibition |
| Group 1 | 79 | 160 | 130 | 115 | 102 | | | | | |
| Group 2 | 81 | 112 | 99 | 89 | 80 | 62 | 65 | 78 | 100 | 77 |
| Group 3 | 80 | 118 | 108 | 94 | 85 | 53 | 45 | 61 | 78 | 59 |
| Group 4 | 81 | 116 | 107 | 98 | 89 | 57 | 49 | 53 | 65 | 56 |

From the result it was observed that group 2 animals fed with turmeric fibre (80%) 50 mg/Kg showed a 77% inhibition in rise in blood glucose level compared to group 3 rats fed with soluble dietary fibre from Guar beans, which showed only 59% inhibition in rise in blood glucose level. Group 4 animals fed with modified starch from Tapioca showed 56% inhibition in rise in blood glucose level.

Example 6

Anti-Inflammatory Study

Anti-inflammatory study of turmeric dietary fibre was conducted in Wistar rats. Rats were divided into 5 groups and orally administered with study samples.

- Group 1: consisted of control animals and were fed with vehicle (1% tween 80)
- Group 2: animals which were given Diclofenac standard (10 mg Diclofenac/Kg body weight)
- Group 3: Animals were given turmeric dietary fibre having 80% total dietary fibre (50 mg/Kg)
- Group 4: Animals were given soluble dietary fibre from Guar beans (50 mg/Kg)
- Group 5: Animals were given modified starch from tapioca (50 mg/Kg)

Then after 30 mins, the treated rats were challenged with carrageenan (0.1 ml, 1% carrageenan suspension in 0.9% NaCl solution) by injecting to the animals in sub plantar region of the hind paw. Carrageenan is a chemical known to induce inflammation in rats. The paw volume was determined for all the animals at different time intervals (base line, 3 hr, 6 Hr) after carrageenan injection using digital plethysmometer and the percentage inhibition of inflammation was calculated using following formula:

$$\text{Percentage inhibition}=(1-D/C)\times 100$$

D-Represents the difference in paw volume from baseline in test/standard group.

C-Represents the difference in paw volume from baseline in the control group.

A higher value of percentage inhibition indicated less paw volume in the animals as compared to control animals and more anti-inflammatory activity.

TABLE 1

Percentage inhibition of inflammation in carrageenan induced paw oedema model

| | 3 Hr | 6 Hr | Average percentage inhibition |
|---|---|---|---|
| Group 1 | 0 | 0 | 0 |
| Group 2 | 46% | 32% | 39% |
| Group 3 | 64% | 57% | 61% |
| Group 4 | 51% | 41% | 46% |
| Group 5 | 44% | 35% | 40% |

As seen in table 1, group 3 animals treated with turmeric fibre with 80% dietary fibre showed 61% inhibition of inflammation compared to group 2 animals treated with standard Diclofenac drug. Group 4 animals treated with soluble dietary fibre from Guar gbeans showed 46% inhibition of inflammation and group 5 animals treated with modified starch from tapioca showed 40% inhibition of inflammation.

Example 7

Bioavailability Study

Study for finding the bioavailability of curcumin, demethoxycurcumin and bisdemethoxycurcumin in the brain of rats by administering a combination of turmeric fibre composition and curcuminoids.

Albino rats weighing 200-250 gm of both sexes were used for the study. The rats were kept individually in polypropylene cages and maintained in well ventilated room under normal and uniform conditions of 12 hours light and dark cycle and at 26+2° C. Water and feed were given ad-libitum. The animals were divided into 4 groups of 3 animals in each group having an oral dosage of 60 mg/Kg. Animals were divided as shown in table 1.

TABLE 1

Animals grouping for Bioavailability study.

| | |
|---|---|
| Group 1 | Vehicle |
| Group 2 | Curcuminoid alone |
| Group 3 | DFC + curcuminoids |
| Group 4 | DFC + bioavailable turmeric formulation |

After 24 hours, rats were killed under ether anaesthesia, and brain was collected. Brain samples were quickly frozen in liquid nitrogen, and stored at −80° C. until analysis by LC-MS.

LC-MS Analysis of Curcuminoids in Brain Sample.

Brain extraction: Brain sample (30 mg) was pulverized and extracted with 2 ml ethyl acetate. Ethyl acetate fraction was collected and repeated the extraction two more times with ethyl acetate. The entire ethyl acetate fraction was combined. After 10 min of vortex and sonication, the suspension was centrifuged at 3,000 rpm for 3 min. The supernatant was evaporated under reduced pressure to form a residue for LC-MS analysis.

Curcuminoids Analysis:

An LC system (Waters, Corporation, Milford, U.S.A) consisting of an Acquity ultra Performance LC and electrospray chemical ionization tandem mass spectrometer (ESCi-MS/MS; Waters) was used. The samples were separated on Ambient BEH C18 (2.1×50 mm), 1.7p or Equivalent L1 column. The calibration curves of bisdemethoxycurcumin, demethoxycurcumin and curcumin were linear over the concentration range of 1-800 ppb. The LOQ for curcumin, demethoxycurcumin and bisdemethoxycurcumin were 10.0 ppb.

The residue was reconstituted with 1 ml of acetonitrile: water containing 0.1% Formic acid (1:1) and transferred into a micro-vial. A 5 μl aliquot was injected in LC-MS/MS system & analyzed the curcuminoids. Data acquisition and quantitation were performed using MassLynx software version 4.1.

GC-MS Analysis of α-Turmerone, β-Turmerone, Ar-Turmerone Analysis:

Turmerone analysis: A GC system (Shimadzu Corporation, Kyoto, Japan) consisting of a GCMS-QP 2010 ultra Gas Chromatograph mass spectrometer and an electron ionization mode was used. The samples were separated on Rxi-5Sil MS (30 m, 0.25 mmID) column.

The residue was reconstituted with 1 ml of hexane and transferred into a micro-vial. A 1 μl aliquot was injected in the GC-MS system & analyzed the alpha, beta & Ar-turmerone. Data acquisition and quantitation were performed using Shimadzu GCMS solution software.

TABLE 2

Curcumin, demethoxycurcumin (DMC), bisdemethoxycurcumin (BDMC), α-turmerone, β-turmerone and Ar-turmerone in the brain.

| Group | Curcumin (ng/mg) | DMC (ng/mg) | BDMC (ng/mg) | α-Turmerone (ng/mg) | β-turmerone (ng/mg) | Ar-turmerone (ng/mg) |
|---|---|---|---|---|---|---|
| Group 1 | 0 | 0 | 0 | 0 | 0 | 0 |
| Group 2 | 2.3 | 0 | 0 | NA | NA | NA |
| Group 3 | 40 | 18 | 6 | NA | NA | NA |
| Group 4 | 125 | 32 | 15 | 8 | 2 | 35 |

The results as shown in Table 2 indicate that animals fed with composition of turmeric fibre and bioavailable turmeric formulation (Group 4) showed high detection of curcumin, demethoxycurcumin, bisdemethoxycurcumin, α-Turmerone, β-turmerone and Ar-turmerone in brain. In the curcuminoid alone group, small detection of curcumin was found. Demethoxycurcumin and bisdemethoxy curcumin were not detected in brain of rats fed with curcuminoids alone. Whereas in group 3 animals fed with composition of turmeric fibre and curcuminoid alone enhances the availability of curcumin, demethoxy curcumin and bisdemethoxycurcumin in rat brain compared to curcuminoid alone group.

Other modifications and variations to the invention are apparent to those skilled in the art from the foregoing disclosure and teachings. The scope of the invention is not limited to the turmeric extract prepared in the above illustrations, a person skilled in the art can use extracts prepared from other known methods. Thus, while only certain embodiments to showcase the applicability of the invention have been specifically described herein, it will be apparent that numerous alterations are possible without departing from the spirit and scope of the invention.

I claim:

1. A dietary fibre composition comprising
at least 40% dietary fibre by weight,
wherein the dietary fibre comprises of soluble fibre and insoluble fibre in a weight ratio of 1:99 to 1:9,
wherein the insoluble fibre comprises resistant starch in an amount of 15 to 75% of the composition,
wherein the resistant starch comprises unmodified starch of type 1 and type 2, and one or more modified starch selected from a group of type 3 type 4, and type 5, wherein the
modified starch and unmodified starch is in a ratio of 1:0.2 to 1:85 by weight; and
wherein the dietary fibre is derived from turmeric.

2. The dietary fibre composition of claim 1, comprising 1 to 10% protein.

3. A composition comprising the dietary fibre composition of claim 1, and one or more additive or excipient selected from the group consisting of: acidulants, antioxidants, sequestrants, colours, colour retention agent, sweeteners, emulsifiers, fats, oils, flavours, flavour enhancers, flour, flour treatment agents, gums, preservatives, stabilizers, spices, thickeners, bulking agents, vitamins, anti-caking agents, antifoaming agents, and humectants; and the excipients are selected from group consisting comprising of: fillers, binders, glidants, lubricants, stabilizers, solubilizers, disintegrants, polymers, sweeteners and flavourants.

4. The composition of claim 1, where in the composition is derived from the plant source by extraction, modification and enrichment.

5. The composition of claim 4, further comprising a plant extract, wherein the plant extract is selected from the group consisting of turmeric, ginger, amaranth, berberin, black pepper, long pepper, green tea, green coffee, pomegranate, grape seeds, Emblica, ashwagandha, boswellia and combination thereof.

6. The composition of claim 4, further comprising micro minerals, vitamins or a combination thereof.

7. A bioavailable formulation comprising the composition of claim 6.

8. The composition of claim 4, further comprising one or more plant nutrients selected from the group consisting of: curcuminoids, withanosides, turmerones, gingerols, Flavone, Quercetin, Genistein, Caffeic Acid, Catechin, Daidzein, Diospyrin, Ellagic Acid, Epicatechin, Etoposide, Ferulic Acid, Geshoidin, Galic Acid, Pumicalagin, Xanthones, Benzophenones, Hydroxycitric Acid, Anthocyanins, Myristicin, Safrole, Eugenol and combinations thereof.

9. A bioavailable formulation comprising the composition of claim 8.

10. The composition of claim 3 in the form of a dietary supplement or a functional food selected from the group consisting of juices, fruit drinks, carbonated beverages, milk, nutritional drinks, ice cream, breakfast cereals, biscuits, cakes, muffins, cookies, candies, bread, toppings, bread, fibre bars, soups, crackers, baby formulae, teas, salad dressings, cooking oils, cheese, butter, jellies, jams or preserves.

11. The composition of claim 3, wherein the composition is a pharmaceutical preparation in a dosage form, and the dosage form is selected from the group consisting of capsule, tablet, mini tablet, granule, sachet, powder, paste, infusion, ampoule, solution, suspension, emulsion, pills, cream, enteric coated formulations, and combinations thereof.

12. The composition of claim 11, wherein the dosage form has a mass in the range of 100 mg to 4000 mg.

13. The dietary fibre composition of claim 1, prepared by a method comprising the steps of:
(a) boiling fresh rhizomes of turmeric in water for 2 hours at 100° C. and followed by cooling;
(b) separate the rhizomes from the water part;
(c) the rhizome of step (b) is extracted with ethyl acetate to obtain ethyl acetate extract and a first residue;
(d) the first residue is separated from ethyl acetate;
(e) the first residue of step (d) is kept in HCl at 50° C. to 70° C. incubation for 12 to 36 hours to form first slurry;
(f) the pH of the first slurry is adjusted about 5 by adding NaOH;
(g) the first slurry is kept at 100° C. incubation for 30 minutes;
(h) after the incubation of step (g) the first slurry is cooled at room temperature for 5 hours;
(i) the first slurry is filtered to obtain a second residue;
(j) the second residue is moistened with steam;
(k) the second residue is cooled to room temperature to form third residue;
(l) enzyme amyloglucosidase is added to the third residue and kept for 10 to 36 hours to form a second slurry;
(m) filter out second slurry from (l) to obtain fourth residue;
fourth residue from step (m) is washed with water and dried to obtain the dietary fibre composition with 75±5% resistant starch.

14. The dietary fibre composition of claim 13, wherein;
(1) the first residue from step (d) is mixed with 5 times the water to form a mixture-1;
(2) pH of the mixture is maintained at 1.5 by adding HCl;
(3) the mixture is kept at 60° C.-100° C. incubation for 4-8 hours to form a slurry-1;
(4) after incubation pH of slurry-1 is adjusted to 6 by adding NaOH to form slurry-2;
(5) Slurry-2 is cooled to room temperature;
(6) slurry-2 is filtered and washed with water to obtain wet residue-1;
(7) residue-1 is mixed with 5 times the water to get mixture-2;
(8) the pH of mixture-2 is maintained at 6 by adding NaOH;
(9) enzyme alpha-Amylase is added in mixture-2 of step (8) and kept for 15 to 60 minute incubation at 80-110° C.;

(10) after incubation period of step (9) the mixture-2 of step (9) is cooled, and pH is adjusted to 7.4 by adding NaOH;

(11) enzyme Protease is added to mixture-2 of step (10) and kept at 60° C. at incubation for 0.5-2 hours;

(12) after the incubation period of step (11) the mixture-2 of step (11) is cooled to room temperature, pH is adjusted to 4.5 by adding HCl;

(13) enzyme Amyloglucosidase is added to the mixture-2 of step (12) and kept at 60° C. incubation for 0.5-2 hours;

(14) after the incubation period of step (13) the mixture-2 of step (13) is cooled to room temperature to form slurry-3;

(15) the slurry-3 from step (14) is filtered to get a residue-2;

(16) the residue-2 from step (15) is washed with water followed by alcohol; and

(17) washed residue-2 from step (16) is dried and powered to obtain dietary fibre composition with 80-95% dietary fibre.

* * * * *